United States Patent [19]
Pifferi et al.

[11] 4,118,396
[45] Oct. 3, 1978

[54] PYRROLIDINE DERIVATIVES

[75] Inventors: Giorgio Pifferi, Milan; Mario Pinza, Corsico (Milan), both of Italy

[73] Assignee: I.S.F. S.p.A., Milan, Italy

[21] Appl. No.: 713,901

[22] Filed: Aug. 12, 1976

[30] Foreign Application Priority Data

Aug. 13, 1975 [IT] Italy ................................ 26326 A/75

[51] Int. Cl.² .......................................... C07D 207/28
[52] U.S. Cl. ................. 260/326.43; 424/274
[58] Field of Search ..................... 260/326.43

[56] References Cited

U.S. PATENT DOCUMENTS 3,577,432  5/1971  Helsley et al. .................. 260/326.43

FOREIGN PATENT DOCUMENTS 1,011,886  7/1957  Fed. Rep. of Germany ...... 260/326.43

OTHER PUBLICATIONS

J. Int. Med. Res. 3, p. 352 (1973).
Arch. Int. Pharmacodyn 210, p. 38 (1974).

*Primary Examiner*—Nicholas S. Rizzo

*Attorney, Agent, or Firm*—Stevens, Davis, Miller & Mosher

[57] ABSTRACT

Pyrrolidin-2-one derivatives of the formula:

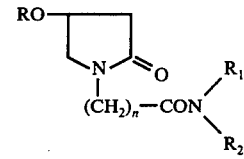

wherein R represents hydrogen, an acyl radical containing from 2 to 7 carbon atoms, a saturated or unsaturated alkyl, containing from 1 to 6 carbon atoms, aralkyl, cycloalkyl or aromatic, $R_1$ and $R_2$ may be the same or different and represent hydrogen, a saturated or unsaturated alkyl radical, containing from 1 to 3 carbon atoms, cycloalkyl radical or $R_1$ and $R_2$, together with the adjacent nitrogen atom, may form an heterocyclic ring optionally containing an additional heteroatom selected from the group consisting of oxygen and nitrogen, $n$ represents an integer from 0 to 2 inclusive, and the process for their preparation are described.

7 Claims, No Drawings

PYRROLIDINE DERIVATIVES

The present invention is concerned with pharmacologically active pyrrolidine derivatives and with the method for their preparation. More particularly the object of the present invention is to produce compounds having the general formula

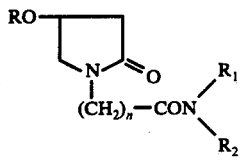

wherein R represents hydrogen, acyl radical containing from 2 to 7 carbon atoms, saturated or unsaturated alkyl containing from 1 to 6 carbon atoms, aralkyl, cycloalkyl or aromatic radical $R_1$ and $R_2$ may be the same or different and represent hydrogen, saturated or unsaturated alkyl radical containing from 1 to 3 carbon atoms, cycloalkyl radical or $R_1$ and $R_2$, together with the adjacent nitrogen atom, may form an heterocyclic ring optionally containing an additional heteroatom such as oxygen and nitrogen, and $n$ represents an integer from 0 to 2 inclusive.

The term acyl radical includes the acyl moiety of aromatic, aliphatic mono- or dicarboxylic acids such as acetic, propionic, butyric, n- valeric, hexanoic, malonic, succinic, benzoic acid and the like. The term alkyl, aralkyl, cycloalkyl and aromatic radical, includes among others, methyl, ethyl, propyl, butyl, cyclopropylmethyl, pentyl, hexyl, allyl, propargyl, benzyl, vinyl, ethynyl, cyclopentyl, cyclohexyl, phenyl and the like. The substituents $R_1$ and $R_2$ may form together with the adjacent nitrogen atom, a piperidine, piperazine, oxazolidine or oxazoline nucleus.

According to the process of the present invention pyrrolidine compounds of formula I, wherein R is an hydrogen atom, are prepared by subjecting compounds of formula II to decarboalkoxylation (a) to form 2,4-diketo compounds of formula III, which in turn are subjected to hydrogenation (b) with formation of 4-hydroxy compounds IV and successive ammonolysis (c) to give final compounds Ia.

The process can be schematically indicated as follows:

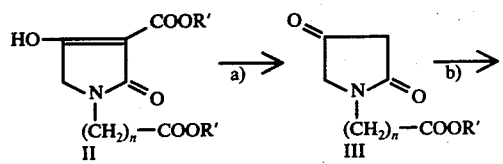

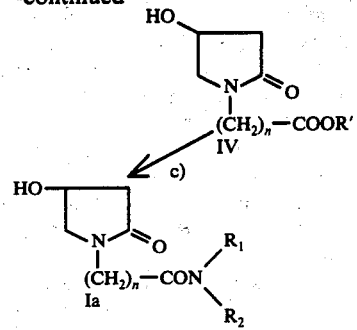

wherein R' represents an alkyl radical containing from 1 to 3 carbon atoms, $R_1$, $R_2$ and $n$ have the above meaning.

In order to obtain those compounds included in formula I wherein R represents acyl, alkyl, aralkyl, cycloalkyl or aromatic radical, compounds of formula Ia coming from step (c) are treated in a known manner with a suitable agent capable of modifying the hydroxy group in position 4 into the desired group. Schematically it may be represented

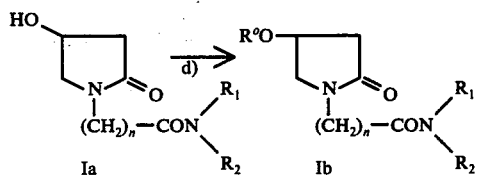

wherein R° represents an acyl radical having from 2 to 7 carbon atoms, a saturated or unsaturated alkyl containing from 1 to 6 carbon atoms, aralkyl, cycloalkyl or aromatic radical while $R_1$, $R_2$ and $n$ have the above meaning.

Alternatively, the sequence of the above reaction scheme may be reversed as to the ammonolysis step (c) and the introduction of the group R° at the hydroxy group in position 4 in step (d). Thus the introduction of the R° group, particularly in these derivatives in which R° represents an unsaturated alkyl containing from 1 to 6 carbon atoms, may be carried out directly on the ester compound IV and then the derivative so obtained submitted to ammonolysis to prepare compounds Ib. The decarboalkoxylation reaction (a) for the new compound of formula II which exists in its keto/enol form, is effected by heating to reflux in a suitable solvent in the presence of water, which is necessary for the hydrolysis of the ester group of the starting product. The so obtained product, represented by formula III, is subjected to hydrogenation (a) with complex hydrides or, alternatively, with hydrogen in the presence of catalysts in suitable solvents. In a preferred embodiment of the process, compound III is treated in an ether solvent or tetrahydrofuran with an approximately stoichiometric quantity of sodium borohydride. The ammonolysis reaction (c) of compound IV is effected according to known techniques, with ammonia or suitable amine of the formula $HNR_1R_2$ in which $R_1$ and $R_2$ have the above meanings, with the exception that $R_1$ and $R_2$ are not both hydrogen.

The compounds of the invention display a very interesting activity on the central nervous system: they were tested in comparison to controls and to the known product, which possesses the closest chemical structure and similar pharmacological behaviour, Piracetam, namely 2-(pyrrolidin-2-on-yl) acetamide. The compounds were tested in accordance with learning and memory screening carried out in the following manner:

(a) Pole climbing test

Male Wistar albino rats from our breeding, 60 days old at the beginning of the experiments were used. The experimental techniques were basically those described by Cook L., Weidley E. F. (Ann. N.Y. Acad, Sci. 66; 740, 1957). The anticipated conditioned response ($CR_2$) described by Maffii G. (J. Pharm. Pharmacol.; 11 129, 1959) was also considered. After the rats were put in the conditioning box, the following schedule was employed: 15 seconds without any stimulation, 15 seconds with acoustic stimulus and 30 seconds with acoustic stimulus plus electrical foot shocks (1.3 m A). Climbing the pole during the first 15 seconds without stimulus is the anticipatory conditioned response $CR_2$, climbing the pole during acoustic stimulus is the conditioned response $CR_1$. The animals were treated by intraperitoneal or by oral route every day for 3 consecutive days one hour before each training session. Every day two training sessions were performed, namely at 9 a.m. and at 4 p.m. The learning rate of both $CR_2$ and $CR_1$ were considered.

(b) Passive avoidance followed by maximal electroshock.

Male albino Swiss mice from our breeding were employed. The mice were 25 days old. The method and the apparatus were essentially those described by Essman W. B. on Psychopharmacologia (Berl) 9; 426, 1966. The passage from a light box into a dark one was punished by foot shock (1.3 m A - 5 sec.). Immediately after the trial a maximal electro convulsive shock (E.C.S.) 30 m A - 150 msec. 50 $H_z$ was given to the mouse by corneal electrodes. Compounds were administerd by intraperitoneal or by oral route 1 hour before the trial. The retest was performed 24 hours after E.C.S. Mice that did not cross from the light box into the dark one in 30 seconds were considered as non-affected by the retrograde amnesic effect of E.C.S.

Control animals were submitted to E.C.S. or sham E.C.S.

Table 1

Learning rate of the conditioned avoidance response $CR_1$

| Compound | dose mg/Kg | route | number of animals | Conditioned animals % Session | | | |
|---|---|---|---|---|---|---|---|
| | | | | 1 | 2 | 3 | 4 |
| Controls (saline) | — | i.p. | 200 | 0 | 25 | 62 | 88 |
| 2-(4-Hydroxypyrrolidin-2-on-1-yl) acetamide | 10 | i.p. | 20 | 0 | 50* | 75 | 90 |
| | 30 | i.p. | 20 | 0 | 60* | 95* | 100* |
| | 10 | os | 20 | 0 | 65* | 80 | 100* |
| | 30 | os | 20 | 0 | 75* | 85* | 100* |
| 2-(4-Acetoxypyrrolidin-2-on-1-yl) acetamide | 10 | i.p. | 20 | 0 | 45* | 70 | 90 |
| | 30 | i.p. | 20 | 0 | 65* | 95* | 100* |
| | 10 | os | 20 | 0 | 55* | 70 | 95 |
| | 30 | os | 20 | 0 | 55* | 85* | 100* |
| Piracetam | 10 | i.p. | 20 | 0 | 40 | 70 | 80 |
| | 30 | i.p. | 20 | 0 | 50* | 80 | 95 |
| | 100 | i.p. | 20 | 0 | 40 | 85* | 95 |
| | 30 | os | 20 | 0 | 30 | 60 | 90 |
| | 100 | os | 20 | 0 | 60* | 90* | 100* |

*significative data

Table 2

Learning rate of the anticipatory conditioned avoidance response $CR_2$

| Compound | dose mg/kg | route | number of animals | Conditioned animals % Session | | | | | |
|---|---|---|---|---|---|---|---|---|---|
| | | | | 1 | 2 | 3 | 4 | 5 | 6 |
| Controls (saline) | — | i.p. | 200 | 0 | 10 | 20 | 40 | 60 | 72 |
| 2-(4-Hydroxypyrrolidin-2-on-1-yl) acetamide | 10 | i.p. | 20 | 0 | 15 | 40* | 60 | 80* | 85 |
| | 30 | i.p. | 20 | 0 | 25* | 65* | 75* | 80* | 95* |
| | 10 | os | 20 | 0 | 20 | 60* | 90* | 75 | 90* |
| | 30 | os | 20 | 0 | 15 | 60* | 70* | 90* | 100* |
| 2-(4-Acetoxypyrrolidin-2-on-1-yl) acetamide | 10 | i.p. | 20 | 0 | 5 | 40* | 55 | 70 | 90 |
| | 30 | i.p. | 20 | 0 | 25* | 60* | 65* | 80* | 80 |
| | 10 | os | 20 | 0 | 30* | 35 | 80* | 85* | 85 |
| | 30 | os | 20 | 0 | 30* | 55* | 90* | 85* | 90 |
| Piracetam | 10 | i.p. | 20 | 0 | 10 | 20 | 60 | 70 | 70 |
| | 30 | i.p. | 20 | 0 | 20 | 40* | 65* | 80 | 85 |
| | 100 | i.p. | 20 | 0 | 40* | 65 | 75* | 80 | 85 |
| | 10 | os | 20 | 0 | 15 | 35 | 50 | 80 | 85 |
| | 30 | os | 20 | 0 | 20 | 55* | 80* | 90* | 85 |
| | 100 | os | 20 | 0 | 30* | 50* | 80* | 90* | 85 |

*significative data

Table 3

| | Passive avoidance + E.C.S. | | | |
|---|---|---|---|---|
| Compound | dose mg/kg | route | number of animals | amnesia % |
| Controls + E.C.S. | saline | i.p. | 125 | 70 |
| Controls sham E.C.S. | saline | i.p. | 100 | 12 |
| 2-(4-Hydroxypyrrolidin-2-on-1-yl) acetamide | 30 | i.p. | 39 | 69 |
| | 60 | i.p. | 68 | 58* |

Table 3-continued

| Compound | Passive avoidance + E.C.S. | | | |
|---|---|---|---|---|
| | dose mg/kg | route | number of animals | amnesia % |
| + E.C.S. | 100 | i.p. | 48 | 44* |
| | 60 | os | 30 | 57* |
| | 100 | os | 30 | 50* |
| 2-(4-Acetoxypyrrolidin-2-on-1-yl) acetamide | 60 | i.p. | 30 | 67 |
| | 100 | i.p. | 40 | 52* |
| + E.C.S. | 60 | os | 40 | 55 |
| | 100 | os | 35 | 48* |
| Piracetam | 60 | i.p. | 30 | 67 |
| + E.C.S. | 100 | i.p. | 30 | 50* |
| | 60 | os | 30 | 63 |
| | 100 | os | 30 | 57* |

*significative data

The following examples are to illustrate the present invention and should not be construed as limiting it.

EXAMPLE 1

2-(4-Hydroxypyrrolidin-2-on-1-yl) acetamide

To a mixture containing 648 g ethyl iminodiacetate in 3600 ml anhydrous methylene chloride and 572 ml triethylamine at 0° C., a solution of 619 g 2-carbethoxyacetylchloride in 1100 ml methylene chloride is added dropwise and under stirring, while checking that the reaction temperature does not exceed 10°–15° C. The mixture is kept under stirring for 2 hours at room temperature and allowed to stand overnight, thereafter washed with water, made anhydrous and evaporated under vacuo. Ethyl N-(2-carbethoxyacetyl)-iminodiacetate, in the form of an oil, is dissolved in anhydrous benzene and added at room temperature to a solution of 75.6 g sodium in 2700 ml of absolute ethyl alcohol. The solution is refluxed for 6 hours, cooled to room temperature, repeatedly extracted with water, the aqueous extracts collected together and acidified to pH 1 with hydrogen chloride, and a precipitate containing 2-(3-carbethoxy-4-hydroxy-$\Delta^3$-pyrrolidin-2-on-1-yl) ethyl acetate, which purified by recrystallization melts at 175°–179° C., is obtained.

Twenty grams of 2-(3-carbethoxy-4-hydroxy-$\Delta^3$-pyrrolidin-2-on-1-yl) ethyl acetate are added to 200 ml warm anhydrous acetonitrile and 1.8 ml water. The mixture is refluxed for about 20 minutes and thereafter cooled on an ice bath and evaporated under vacuo to give 2-(pyrrolidino-2,4-dion-1-yl) ethyl acetate melting at 87°–91° C.

To 22.25 g 2-(pyrrolidino-2,4-dion-1-yl) ethyl acetate in 445 ml anhydrous dimethoxyethane cooled to 0° C., 1.52 g sodium borohydride are added; the mixture is allowed to stand for 10 minutes on an ice bath and then for 30 minutes at room temperature. The solution is acidified with 20% hydrochloric acid, filtered in vacuo, evaporated in vacuo, taken up with methylene chloride and made anhydrous over magnesium sulphate; by filtration and evaporation, in vacuo and successive chromatography 2-(4-hydroxy-pyrrolidin-2-on-1-yl) ethyl acetate having a boiling point of 180° C. (with decomposition) is separated.

To a solution of 8.9 g 2-(4-hydroxypyrrolidin-2-on-1-yl) ethyl acetate in 300 ml methyl alcohol is added at 0° C. gaseous ammonia and is then allowed to stand overnight. The solvent is removed in vacuo, the residue is taken up with methyl alcohol, filtered over charcoal, and slowly added to 200 ml isopropyl ether. 2-(4-Hydroxypyrrolidin-2-on-1-yl) acetamide melting at 161°–163° C. precipitates.

EXAMPLE 2

2-(4-Acetoxypyrrolidin-2-on-1-yl) acetamide

A mixture of 5.53 g 2-(4-hydroxypyrrolidin-2-on-1-yl) acetamide and 44.3 ml acetyl chloride is refluxed for 15 minutes. It is then cooled, the solvent is evaporated in vacuo and the residue oil taken up with a small quantity of aqueous sodium bicarbonate, and solid sodium bicarbonate is added under stirring until neutrality. Most of the water contained in the mixture is removed by treatment in vacuo with methylisobutylketone, the residue is taken up with methylene chloride, made anhydrous over sodium sulphate and evaporated in vacuo. The residue oil is slurried into isopropyl alcohol/ethyl ether and crystallized from isopropyl alcohol/isopropyl ether (20:80) to obtain 2-(4-acetoxypyrrolidin-2-on-1-yl) acetamide, which purified by chromatography melts at 84°–86° C.

EXAMPLES 3–7

In accordance with the process of the invention as described above the following compounds were prepared:

2-(4-Methoxypyrrolidin-2-on-1-yl) acetamide melting at 104°–105° C.

2-(4-Allyloxypyrrolidin-2-on-1-yl) acetamide melting at 111°–112° C.

2-(4-Benzoyloxypyrrolidin-2-on-1-yl) acetamide melting at 155°–156° C.

N-ethyl-(4-benzoyloxypyrrolidin-2-on-1-yl) carboxamide melting at 79°–80° C.

2-(4-Hydroxypyrrolidin-2-on-1-yl) propionamide melting at 98°–100° C.

We claim:
1. 2-(4-Hydroxypyrrolidin-2-on-1-yl) acetamide.
2. 2-(4-Acetoxypyrrolidin-2-on-1-yl) acetamide.
3. 2-(4-Methoxypyrrolidin-2-on-1-yl) acetamide.
4. 2-(4-Allyloxypyrrolidin-2-on-1-yl) acetamide.
5. 2-(4-Benzoyloxypyrrolidin-2-on-1-yl) acetamide.
6. N-ethyl-(4-benzoyloxypyrrolidin-2-on-1-yl) carboxyamide.
7. 2-(4-Hydroxypyrrolidin-2-on-1-yl) propionamide.

* * * * *

UNITED STATES PATENT AND TRADEMARK OFFICE
CERTIFICATE OF CORRECTION

PATENT NO. : 4,118,396
DATED : October 3, 1978
INVENTOR(S) : Giorgio Pifferi et al.

It is certified that error appears in the above—identified patent and that said Letters Patent are hereby corrected as shown below:

Column 3, line 3, "2-(pyrrolidin-2-on-yl)" should read
-- 2-(pyrrolidin-2-on-1-yl) --.

Signed and Sealed this

Tenth Day of July 1979

[SEAL]

Attest:

LUTRELLE F. PARKER
Attesting Officer — Acting Commissioner of Patents and Trademarks

UNITED STATES PATENT AND TRADEMARK OFFICE
CERTIFICATE OF CORRECTION

PATENT NO. : 4,118,396
DATED : October 3, 1978
INVENTOR(S) : Giorgio Pifferi and Mario Pinza It is certified that error appears in the above-identified patent and that said Letters Patent are hereby corrected as shown below:

Column 6, line 52 (Example 7), change "2-(4-Hydroxypyrrolidin-2-on-1-yl) to -- 3-(4-Hydroxypyrrolidin-2-on-1-yl)--

Column 6, line 62 (Claim 7), change "2-(4-Hydroxypyrrolidin-2-on-1-yl) to -- 3-(4-Hydroxypyrrolidin-2-on-1-yl)--

Signed and Sealed this

Tenth Day of June 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,118,396
DATED : October 3, 1978
INVENTOR(S) : Giorgio Pifferi and Mario Pinza It is certified that error appears in the above–identified patent and that said Letters Patent are hereby corrected as shown below:

Column 5, line 37 (Example 1), change "carbethoxy-4-hydroxy-$\Delta^3$-pyrrolidin-2-on-1-yl) to
-- carbethoxy-4-hydroxy-$\Delta^3$-pyrrolin-2-on-1-yl --;

Column 5, line 41 (Example 1), change "rolidin-2-on-1-yl" to -- rolin-2-on-1-yl --.

Signed and Sealed this

Ninth Day of September 1980

[SEAL]

Attest:

SIDNEY A. DIAMOND

Attesting Officer     Commissioner of Patents and Trademarks